United States Patent [19]

Bunnell et al.

[11] Patent Number: 4,471,773

[45] Date of Patent: Sep. 18, 1984

[54] APPARATUS AND METHOD FOR DELIVERING MEDICATION TO PATIENT'S RESPIRATORY SYSTEM

[75] Inventors: J. Bert Bunnell; Chris G. Faddis, both of Salt Lake City, Utah

[73] Assignee: Bunnell Life System, Inc., Salt Lake City, Utah

[21] Appl. No.: 467,784

[22] Filed: Feb. 18, 1983

Related U.S. Application Data

[63] Continuation-in-part of Ser. No. 322,742, Nov. 19, 1981.

[51] Int. Cl.$^3$ .......................................... A61H 31/00
[52] U.S. Cl. ......................... 128/204.21; 128/200.21; 128/200.16
[58] Field of Search ................... 128/200.14, 200.16, 128/200.21, 201.28, 203.12, 205.24, 203.14, 204.21, 204.17, 204.18

[56] References Cited

U.S. PATENT DOCUMENTS

| | | | |
|---|---|---|---|
| 3,362,404 | 1/1968 | Beasley | 128/200.21 |
| 3,523,527 | 8/1970 | Foster | 128/204.21 |
| 3,826,255 | 7/1974 | Havstad et al. | 128/200.21 X |
| 3,842,828 | 10/1974 | Bird | 128/200.14 |
| 4,265,237 | 5/1981 | Schwanbom et al. | 128/205.24 X |
| 4,279,250 | 7/1981 | Valents et al. | 128/200.14 |
| 4,319,155 | 3/1982 | Nakai et al. | 128/200.16 X |
| 4,351,329 | 9/1982 | Ellestal et al. | 128/205.24 |
| 4,380,233 | 4/1983 | Caillot | 128/204.21 |

Primary Examiner—Edward M. Coven
Attorney, Agent, or Firm—Thorpe, North & Western

[57] ABSTRACT

Apparatus and method are disclosed for delivering medication into the respiratory system of a person. The medication to be delivered is nebulized and supplied, with a series of gas pulses, to a person's respiratory system. The frequency rate of the pulses varies over a range which is broad enough to encompass the natural or resonant frequencies of the person's respiratory system.

14 Claims, 1 Drawing Figure

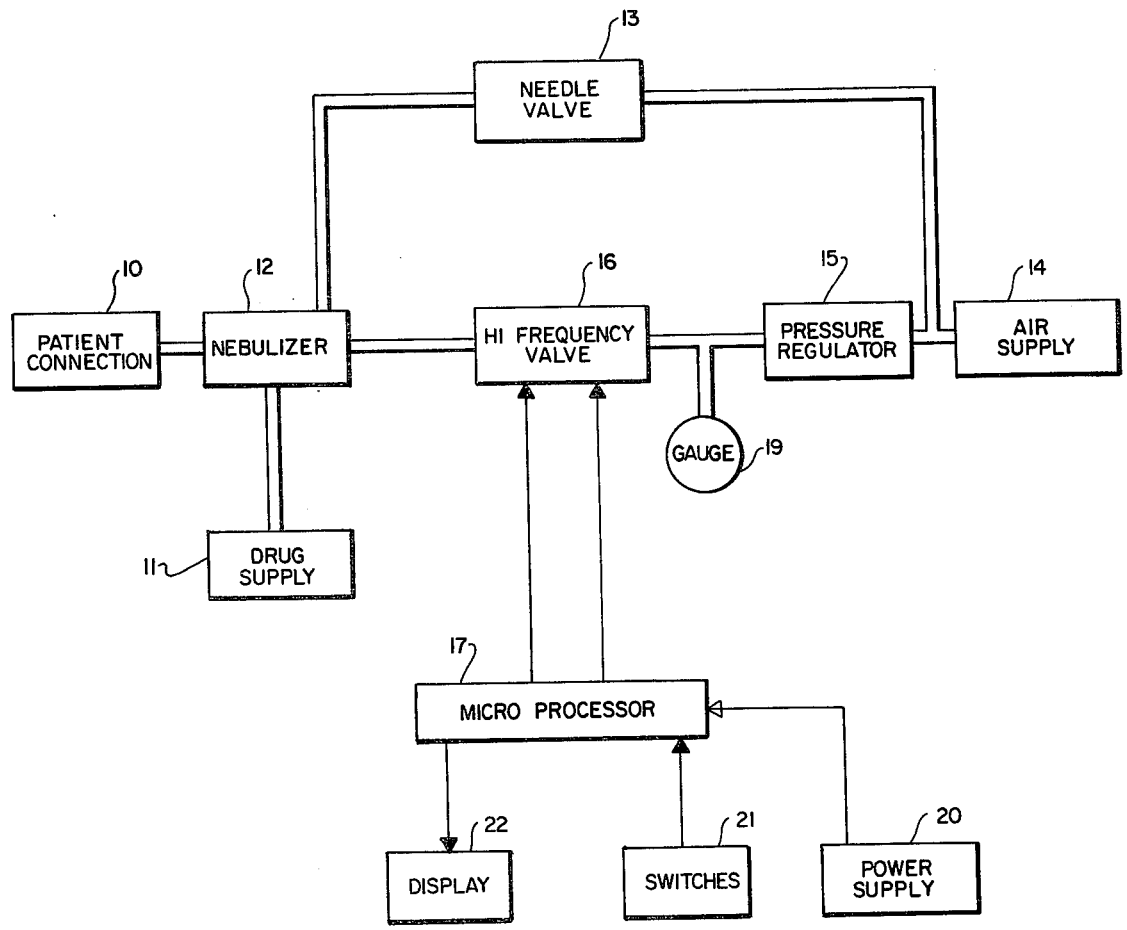

APPARATUS AND METHOD FOR DELIVERING MEDICATION TO PATIENT'S RESPIRATORY SYSTEM

This application is a continuation-in-part of my application Ser. No. 322,742, filed Nov. 19, 1981, for Apparatus and Method for Assisting Respiration.

BACKGROUND OF THE INVENTION

The present invention relates to a new and improved method and apparatus for delivering medication into the respiratory system of a person.

It is well known in the treatment of patients with various respiratory problems to deliver drugs or medication to a person's respiratory system by means of a nebulizer which transforms a liquid medication to a mist and then propels it into the person's nose or throat where it may be inhaled into the lungs. A variety of devices have been developed for this purpose, the simplest being the well known hand-held atomizer operated by a patient squeezing a bulb to produce a jet of air which nebulizes the medication and propels it into the patient's nose or mouth. Other devices, such as the Pulmo-Aide manufactured by the DeVilbiss Co. utilize a compressor for generating a supply of air under constant pressure. Using this with a valve controlled nebulizer, the patient can administer either a continuous or intermittent aerosol under controlled pressure to penetrate into the respiratory system.

For treatment of chronic obstructive lung diseases, such as asthma, bronchitis, emphysema, silicosis, etc., an intermittent positive pressure breathing system has been developed by Monaghan Division of Sandoz, Inc. This system delivers air into the lungs up to a prescribed pressure. When the pressure in the lungs reaches a predetermined level the system shuts off, allowing the patient to breathe freely. The system automatically follows the patients rate of breathing. A nebulizer attachment is provided for adding medication to the air delivered by the system to the patient. The nebulizer works continuously or intermittently, i.e., only during the patients inhalation cycle, as desired.

The prior known devices have been effective in the treatment of many diseases and conditions, but have a common shortcoming in that the medication is deposited along the larger airways but does not penetrate into the smaller passages of the patient's respiratory system. These devices also preferentially deliver medication to the healthier, well ventilated areas of a sick person's lung while it would be more beneficial if the less healthy areas of the lungs could receive more medication.

SUMMARY OF THE INVENTION

It is an object of the invention to provide a new and improved method and apparatus for delivering medication throughout a patient's respiratory system.

It is another object of the invention to provide such a method and apparatus for applying high frequency positive pulses of medication to a person's respiratory system to disseminate the medication throughout the system.

It is a further object of the invention to provide such a method and apparatus for delivering medication to the less healthy, less well ventilated areas of a patient's lungs.

It is an additional object of the invention to apply pulses of medication to a person at frequencies which correspond to the various natural or resonant frequencies of the different parts of the person's respiratory system.

The above and other objects are realized in the present invention by provision of a method and apparatus for applying a series of pulses of medication to a person's respiratory system at a frequency rate which varies over a range which is broad enough to encompass the natural or resonant frequencies of a person's respiratory system.

BRIEF DESCRIPTION OF THE DRAWINGS

The above and other objects and advantages of the present invention will become apparent from a consideration of the following detailed description presented in connection with the accompanying drawings in which:

FIG. 1 is a schematic of apparatus for delivering medication to a person's respiratory system according to the present invention.

DETAILED DESCRIPTION

In the present invention, the gas flow to the nebulizer which serves as the carrier for the medication is supplied in high frequency pulses rather than continuously. For a given level of gas pressure the use of high frequency pulses extends the degree and extent of penetration into the respiratory system beyond that attainable with low frequency pulses or a continuous flow. Therefore the medication can be delivered throughout the respiratory system and particularly to the smaller passages thereof without the use of high pressure which could injure the tissues of the system.

As illustrated in FIG. 1, the patient connector 10 is provided for directing the high frequency pulses of medication into the patient's nose or mouth. In practice this could be a tube or a conventional duck bill attachment which is adapted to be clenched between the patient's lips or teeth. A drug supply 11 is connected to a nebulizer 12 which is in turn connected to the patient connector 10. The nebulizer 12 transforms the liquid drug from the supply 11 to a gas or mist for delivery to the patient and can be any of a number of commercially available products, such as the Guardian Nebulizer sold by the Vix Breathing Equipment Co.

A supply of high pressure air or oxygen is provided at 14 and is connected in series with a conventional pressure regulator 15, a high frequency valve 16 and the nebulizer 12. A needle valve 13 is connected between the air supply 14 and the nebulizer 12 to provide a constant flow of gas at reduced pressure to the nebulizer. This flow, which is referred to as the nebulizer bias, is sufficient to entrain or atomize the medication from the drug supply 11. The pressure of the gas from the supply 14 is reduced to the desired level (below 30 psi) by the regulator 15. High frequency pulses of gas are provided by valve 16 to the nebulizer 12 to provide impetus to the atomized medication for delivery to the patient. The gas pulses are produced by valve 16 which is cycled open and closed at a high frequency in response to signals from a microprocessor 17. Valve 16 may be a conventional fluid control valve such as Model C-20 produced by Precision Dynamics, Inc.

A gauge 19 is connected between the pressure regulator and the valve 16 to provide a visual indication of the gas pressure. The microprocessor is energized by a power supply 20 and is operated in response to input switches 21. A display 22 is connected to the microprocessor to provide a visual display of the various inputs and outputs of the microprocessor. The microprocessor is programmable to produce the various signals desired by the user and may be any of a number of suitable devices, such as the Motorola 6801.

The method of the present invention contemplates varying the frequency of the gas pulses supplied to the patient over some range of frequencies. The range of frequencies over which the gas pulses would be varied is selected to ensure that the natural or resonant frequency of a patient's respiratory system falls within that range. It has been found that a person's respiratory system has a natural or resonant frequency and that various parts of the respiratory system also have their own natural frequencies. See, for example, Dubois, A. B., Brady, A. W., Lewis, D. H., and Burgess, B. F., "Oscillation Mechanics of Lungs and Chest in Man", *Jour. of App. Physiology,* 8, 587 (1956) and Peslin, R., "Theoretical Analysis of Airway Resistances on an Inhomogeneous Lung", *Journal of App. Physiology,* 24, 761 (1968). By sweeping over a range of frequencies, such as from 2 to 30 Hertz, the gas pulses will be supplied to the patient at the natural frequency of the patient's respiratory system at least some of the time, and also at the natural frequencies of various subparts of the respiratory system at least some of the time. Advantageously, the natural frequency of a person's respiratory system would be determined before treatment (for example by using the method described in Williams, S. P., Fullton, J. M., Tsai, M. J., Pimmel, R. L., and Collier, A. M.., "Respiratory Impedance and Derived Parameters in Young Children by Forced Random Noise", *Jour. of App. Physiology: Respiratory, Enviromental and Exercise Physiology,* 47(1), 167 [1979] and then the range of frequencies would be centered about this natural frequency to sweep, for example, between 5 to 10 Hertz below the natural frequency and 5 to 10 Hertz above the natural frequency. By supporting gas pulses to a person's respiratory system at or near the system's natural frequency, less reactance is encountered, and thus a lower positive pressure may be used to provide the gas pulses. Also, better ventilation of the respiratory system is achieved when the pulses are supplied at or near the natural frequency.

Advantageously, the inhale/exhale or open/close ratio (time the valve 16 is open relative to the time the valve is closed) is between 1/1 to 1/10. It has been found that providing a ratio in this range yields satisfaction in delivering medication into the respiratory system of a person. The inhale/exhale ratio is determined by the microprocessor 17 which simply opens the valve 16 for a predetermined period of time, e.g. 0.015 secs., and then closes it for a certain period of time, e.g., from 0.015 to 0.150 secs.

The apparatus herein described may be used as a separate system for treatment or, if desired, may be combined with the apparatus disclosed in my copending application.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

I claim:

1. Apparatus for delivering medication throughout a person's respiratory system including means for nebulizing the medication, means for generating a series of gas pressure pulses, means for automatically varying the frequency of occurrence the gas pulses over a selected range, means for adding the nebulized medication to the gas pulses, and means for supplying the medication pulses to the person's respiratory system.

2. The apparatus of claim 1 in which the generating means includes a source of pressurized gas, and a valve connected between the source and the nebulizing means, said valve being adapted to open and close in response to signals.

3. The apparatus of claim 2 wherein the varying means includes means for producing said signals at a frequency which automatically varies over a selected range and for applying the signals to the valve.

4. The apparatus as in claim 3 wherein said varying means produces signals to cause the valve to open and close for an open/close ratio of from 1/1 to 1/10.

5. The apparatus of claim 4 wherein the generating means includes means for regulating the pressure of the gas supplied to the valve.

6. The apparatus of claim 5 which includes means for supplying a continuous flow of gas to the nebulizing means for nebulizing this medication.

7. The apparatus of claim 1 wherein the varying means includes means for periodically varying the frequency of the gas pulses over selectable ranges.

8. The apparatus of claim 7 wherein said periodic varying means includes means for changing the periodicity of said frequency variation.

9. The apparatus of claim 1 wherein the frequency of gas pressure pulses is varied over a range of approximately 2 Hertz to 40 Hertz.

10. A method of applying medication throughout a person's respiratory system comprising the steps of: nebulizing the medication, producing a series of gas pressure pulses, automatically varying the frequency of occurrence of the gas pulses over a selected range of frequencies which includes the natural frequency of the person's respiratory system, adding the nebulized medication to the gas pulses, and supplying the medication pulses to the person's respiratory system.

11. The method of claim 10 including the step of regulating the pressure of the gas pressure pulses.

12. The method of claim 11 wherein the frequency of gas pressure pulses is automatically varied over a range of approximately 2 Hertz to 40 Hertz.

13. The method of claim 11 wherein the periodicity of frequency variation is selectively changed.

14. The method of claim 10 wherein the ratio of gas pressure pulse duration to time between pulses is from 1/1 to 1/10.

* * * * *